United States Patent [19]

Peel et al.

[11] 4,289,728

[45] Sep. 15, 1981

[54] IMPROVEMENTS IN METHODS OF STERILIZATION

[75] Inventors: John L. Peel; William M. Waites, both of Norwich, England

[73] Assignee: National Research Development Corp., London, England

[21] Appl. No.: 109,317

[22] Filed: Jan. 3, 1980

[30] Foreign Application Priority Data

Jan. 11, 1979 [GB] United Kingdom ............... 1091/79

[51] Int. Cl.³ .................. A61L 2/10; B65B 55/08
[52] U.S. Cl. ........................................ 422/24; 422/28
[58] Field of Search .................... 422/24, 13, 28

[56] References Cited

U.S. PATENT DOCUMENTS 4,012,321  3/1977  Koubek .................. 210/63

FOREIGN PATENT DOCUMENTS 2138032  12/1972  France .
2176504  11/1973  France .
 361636   6/1962  Switzerland .
 605421   9/1978  Switzerland .

OTHER PUBLICATIONS

Doudney, Mutation Research 6 (1968), pp. 345–353.

Powers, *Inter. J. of Radiat. Biol.*, 1972, vol. 22, No. 3, pp. 237–243.

Boucher, *American Jour. of Hospital Pharmacy*, vol. 1, Aug. 29, 1972.

King et al., *J. Appl. Bact.*, 32 pp. 481–490 (1969).

Cerny, *Verpackungs-Rundschau* 28 (1977) Nr. 10, Techn.-wiss. Beillage, S. 77–82.

Hartman et al., *Journal of Bacteriology*, Feb. 1978, pp. 769–774.

Buchner, Robert Bosch GmbH, *Geschaftsbereich Verpackungsmachinen*, Waiblingen, Central Research & Development.

*Primary Examiner*—Ronald Serwin
*Attorney, Agent, or Firm*—Oblon, Fisher, Spivak, McClelland & Maier

[57] ABSTRACT

A method of sterilization which comprises treating a microorganism with an ultraviolet irradiated solution of hydrogen peroxide, the wavelength of the ultraviolet radiation being wholly or predominantly below 325 nm and the concentration of the hydrogen peroxide being no greater than 10% by weight and such that the microorganism is rendered non-viable by synergism between the radiation and the hydrogen peroxide. The invention is particularly applicable to the treatment of spores contaminating food packaging.

18 Claims, No Drawings

IMPROVEMENTS IN METHODS OF STERILIZATION

This invention relates to a method of sterilisation in which a microorganism is rendered non-viable.

At present food packaging is sterilised by treatment with a solution of hydrogen peroxide. Certain strains of microoganisms are however resistant to such treatment and a small, though significant, number of spores survive with consequent risk of spoilage to the contents.

A method of sterilisation has now been found which reduces the number of surviving spores of resistant organisms more efficiently.

According to the present invention a method of sterilisation comprises treating a microorganism with an ultraviolet irradiated solution of hydrogen peroxide the wavelength of the radiation being wholly or predominantly below 325 nm and the concentration of the hydrogen peroxide solution being no greater than 10% by weight and such that the microorganism is rendered non-viable by synergism between the radiation and hydrogen peroxide.

The concentration of the solution of hydrogen peroxide, which is usually aqueous, generally does not exceed 6% by weight and preferably does not exceed 3.0% by weight. The concentration is normally at least 0.01% by weight, a concentration at least 0.25% by weight being preferred especially when the microorganism is present in the form of spores, and a concentration at least 0.5% especially so.

In general the wavelength of the ultraviolet radiation is wholly or predominantly below 300 nm and is usually at least 200 nm. In practice radiation is normally provided from a source having a peak intensity below 325 nm, particularly at 254 nm. The energy of the radiation emitted at the source is normally at least 300 microwatts/cm$^2$, particularly at least 500 microwatts/cm$^2$. Although the intensity of the radiation with which the solution is treated may be established by simple experiment, it is normally at least 75 and preferably at least 150 microwatts per cm$^2$.

Although spores of many microorganisms are destroyed by treatment as hereinbefore described at ambient temperatures, it may be desirable, particularly when treating especially resistant microorganisms, to maintain the solution at an elevated temperature either during irradiation or subsequent thereto. In general, such temperatures do not exceed 120° C. and may not exceed 100°. The temperature, at least when treating resistant organisms, is usually however at least 85° C.

The method of the present invention is applicable to a wide variety of microorganisms, including moulds, yeasts, bacteria, viruses and protozoa and finds particular application in the destruction of spore-forming bacteria, especially those which are dairy contaminants.

Although microorganisms in vegetative form may be treated, the present invention is of particular interest for the destruction of spores, especially those of resistant Bacillus and Clostridium strains, e.g. strains of B. subtilis and B. stearothermophilus such as B. subtilis (ATCC 9372) and B. stearothermophilus (NCDO 1096)

In genral, the irradiation period increases with the resistance of the organism, at least 10 sec. generally being required. Heating of the solution, which may, as hereinbefore indicated, be conducted synchronously with irradiation or subsequent thereto is normally carried out for at least 10 sec. and periods of at least 30 sec., e.g. 60 sec. or more may be desirable.

Although the present method may be applied to sterilisation of liquids, e.g. waste water and cannery cooling water, it is of particular interest for the sterilisation of surfaces, for example surfaces of walls and furniture in hospitals and the surfaces of food containers. The latter surfaces may be treated with the peroxide solution, for example by passing the container or material from which the container is fabricated through a tank containing the solution or by spraying the walls of the container or the material with solution. Irradiation may be carried out by a lamp so disposed that containers or packaging materials which have emerged from the tank or spray are subjected to the method of the present invention.

The synergistic action of the present method on the microorganisms i.e. the action of the radiation and hydrogen peroxide additional to their purely additive effect is illustrated by the following Examples when taken with the comparison experiments.

EXAMPLES 1-71

ORGANISMS

The strains of Bacillus and Clostridium (Examples 1-40), of non-sporing bacteria (Examples 41-69) and of moulds (Examples 70-71) and where appropriate the origins thereof are listed in Table 1.

The following abbreviations apply:
NIRD—National Institute of Research in Dairying, Shinfield, Reading, UK.
NCDO—National Collection of Dairy Organisms
ATCC—American Type Culture Collection
NCIB—National Collection of Industrial Bacteria
FRI—Argicultural Research Council Food Reserach Institute, Colney Lane, Norwich, UK.

TABLE 1

| Strain | Source |
| --- | --- |
| B. subtilis 713 (NCDO 2130) | Bulk milk tank, Iran |
| B. subtilis 738 (NCDO 738) (ATCC 9372) | |
| B. subtilis 706 (NCDO 2129) | Rinse of farm bulk milk tank |
| B. subtilis var. niger (NCIB 8058) | |
| B. subtilis SA22 | R. T. Toledo et al, Appl. Microbiol. 26, 592-7 1973 |
| B. globigii B17 (NCIB 8649) | |
| B. licheniformis 100 | 'In-line' milk |
| B. licheniformis 117 | B. licheniformis T of O. Cerf & J. Hermier Le Lait 52, 1-20 1972 |
| B. licheniformis 109 2AO | UHT spoiled milk, O. Cerf & F. Metro J. Appl. Bacteriol. 42, 405-415, 1977 |
| B. cereus 818 | 'In can' milk |
| B. cereus T | G. J. Dring & G. W. Gould in Spores VI pp 488-494 Ed. Gerhardt P. Costilow R. N. & Sadoff, H. Washington DC American Society for Microbiology 1975 |
| B. pumilus 312 | B. pumilus EJ of O. Cerf & J. Hermier Le Lait 52, 1-20, 1972 |
| B. stearothermophilus 202 (NCDO 1096) | |
| G 12 Clostridium sporogenes PA 3679 (NCIB 8053) | Pond mud |
| Escherichia coli K12 | FRI |

| Strain | Source |
|---|---|
| *Streptococcus faecalis* ss liquefaciens EB/F/30/39 | Chicken gut |
| *Serratia marcescens* (NCTC 10211) | |
| *Penicillium chrysogenum* | UHT spoiled milk |

SPORE PREPARATION AND MAINTENANCE OF CULTURES

*C. sporogenes* is maintained in Robertson's cooked meat medium; the other strains used are maintained on slopes of Oxoid nutrient agar. Spores are produced by growth on one of the following: (i) the potato agar of Gould, Stubbs & King (1970) for *B. subtilis* var. *niger* (ii) Oxoid nutrient agar for *B. stearothermophilus* 202, (iii) the agar medium of Wang, Scharer & Humphrey (1964) for *B. licheniformis* 109 2AO (iv) a medium containing (g/l), Oxoid nutrient broth No. 2 (3.1), $MnSO_4.4H_2O$ (0.03), $K_2HPO_4$ (0.25) and New Zealand Agar (15) for strain G12, (v) a medium containing (g/l); Oxoid skim milk powder (50), Difco yeast extract (3.0), Oxoid peptone (5.0), BBL trypticase (5.0), $MnCl_2.4H_2O$ (0.072) BDH cysteine hydrochloride (0.5), Davis agar (15); the medium is adjusted to a final pH of 7.0 to 7.2 with 1 M-NaOH and spores produced under $H_2:CO_2$ (9:1) for *C. sporogenes* PA 3679, (vi) Bacillus spore agar as described by Franklin et al (1970) with Oxoid Lab Lemco added at 0.1% (w/v) for all other strains. Growth is at 30° C. for *B. subtilis* var. *niger*, *B. subtilis* 738, *B. globigii* B17, strain G12, *B. cereus* T and *B. cereus* 818, at 33° C. for *C. sporogenes* PA 3679, at 37° C. for *B. pumilus* 312, *B. subtilis* SA22, *B. subtilis* 713, *B. subtilis* 706, *B. licheniformis* 100, *B. licheniforms* 117 and *B. licheniformis* 109 2AO or at 55° C. for *B. stearothermophilus* 202.

Spores of *B. stearothermophilus* 202 are produced on 30 ml slopes in 100 ml screw-capped bottles; those of other strains on agar in Petri dishes. Sporulation is detected by the appearance of bright spores by phase contrast microscopy and incubation continued until the highest percentage of free spores is observed (after one to nine days, depending on strain). The cultures are harvested and washed 5 times with sterile glass-distilled water before storage at $-18°$ C.

PREPARATION OF CELLS OF NON-SPORING BACTERIA AND MAINTENANCE OF CULTURES

Non-sporing bacteria are grown at 33° C. in (i) heart infusion broth for *E. coli* and *S. faecalis* (ii) glycerol-salts medium as described by Dimmick (1965) for *S. marcescens* on a gyratory shaker (Gallenkamp, 150 rev/min) for 18 hours. The cells are harvested and washed with 50 ml sterile 25 mM-potassium phosphate buffer pH 7.0 by centrifugation before resuspension at a density of about $1 \times 10^9$ viable units/ml and were used within 4 hours. Cultures are maintained on slopes of Heart Infusion Agar (Difco).

PREPARATION OF MOULD SPORES AND MAINTENANCE OF CULTURE

Spores of *Penicillium chrysogenum* are grown on slopes of Czapek Dox Agar containing (g/l); sucrose (30), $K_2HPO_4$ (1.0), $NaNO_3$ (2.0), $MgSO_4.7H_2O$ (0.5), KCl (0.5) $FeSO_4.7H_2O$ (0.01), and New Zealand Agar (20) at 20° C. for at least 7 days before harvesting in sterile glass distilled water containing 0.1% Tween 80 and washing by centrifuging with sterile glass distilled water. Cultures were also maintained on Czapek Dox Agar.

U.V. IRRADIATION OF BACTERIAL SPORES, VEGATATIVE CELLS AND MOULD SPORES.

Bacterial spores or vegetative cells at $3 \times 10^7$ to $5 \times 10^8$/ml and mould spores at $1 \times 10^6$ ml are suspended in 0.1 M sodium phosphate buffer pH 7.0 and up to 2.5 g/100 ml $H_2O_2$ (Analar, B.D.H.). Volumes of 4 ml are rocked gently to and fro for 30 sec. at 20° C. in a Petri dish base with a diameter of 9 cm at distances of 5.5, 30 cm or 33 cm from an Hanovia Chromatolite low-pressure Hg lamp (Hanovia Ltd., Slough, England) from which the filter is removed as described by W. M. Waites & B. A. Fry *J. Gen. Microbiol* 34, 413–426 (1964). The lamp emits radiation in the range 185–579 nm with a peak intensity at 254 nm; the latter radiation is the only radiation of significant practical value produced by the lamp, the other spectral lines and groups being of much lower intensity. The energy emitted is 300–500 microwatts/sq. cm. at source. Samples (2 ml) are removed and mixed with a filter sterilised solution (2 ml) of catalase (Sigma Ltd) at 7650 units/ml at 20° C. before storing in ice for at least 5 min., dilution and plating.

HEAT TREATMENT (Examples 2–16, 33–35, 31–41, 61 and 71)

Samples (2 ml) are heated to 85° C. in 60 sec., (bacterial spores), 65° C. in 30 sec. (vegetative bacteria) or 54° in 15 sec. (mould spores) by adding to pre-heated screwcapped bottles before adding 2 ml of catalase pre-cooled to $+1°$ C. and containing 7650 units/ml and plunging into ice. The suspensions are stored in ice for at least 5 min. before diluting and plating.

DETERMINATION OF SURVIVORS

Diluted spore suspensions are plated on (i) Bacillus spore agar and incubated for 2 days at 30° C. (*B. subtilis* 713, *B. subtilis* 706, *B. cereus* T and *B. cereus* 818) or 37° C. (*B. licheniformis* 109 2AO, *B. licheniformis* 100, *B. licheniformis* 117 and *B. pumilus* 312); (ii) plate count agar (Oxoid) and incubated for 2 days at 33° C. (*B. subtilis* SA 22) or 2 days at 37° C. (*B. globigii* B17, *B. subtilis* 738 and *B. subtilis* var. niger); (iii) a medium containing (g/l); tryptone (Oxoid) (5): yeast extract (Oxoid) (2.5), glucose (10) and New Zealand Agar (28) and incubated for 3 days at 55° C. (*B. stearothermophilis* 202) (iv) a medium containing (g/l): tryptone (Oxoid) (10), glucose (5.0) and New Zealand Agar (12) and incubated for 2 days at 30° C. (G12) or (v) the reinforced Clostridial medium agar of Hirsch & Grinsted (1954) but with 1.6% New Zealand Agar in place of 1.2% (*C. sporogenses* PA 3679).

Suspensions of vegetative cells are enumerated by diluting 100-fold in maintenance medium (Difco Bactopeptone), 1.0 g/l; NaCl, 5.0 g/l; adjusted to pH 7.0–7.1) and plating on Heart Infusion Agar (Difco) (*E. coli* and *S. faecalis*) or Trypticase Soy agar (BBL) (*S. marcescens*) using a Spiral Plate Maker (Spiral Systems, Cincinnati, Ohio, USA) (Gilchrist et al 1973, Jarvis et al 1977) and colonies counted after 3 days incubation at 33° C. (*S. faecalis*), 2 days incubation at 30° C. (*E. coli*) or 33° C. (*S. marcescens*).

Suspension of mould spores are enumerated by diluting in sterile glass distilled water, plating on Czapek Dox Agar and colonies counted after 9 days incubation at 20° C.

Full references to the publications hereinbefore cited are as follows:

Dimmick R. C. (1965) *J. Bacteriology* 89, 791–798.
Gilchrist, J. E., Campbell, J. E. Donnelly, C. B., Peeler, J. T. & Delaney, J. M. (1973) *Applied Microbiol.* 25, 244–252
Jarvis, B. Lach, V. H. & Wood J. (1977) *J. Applied Bacteriol* 43/, 149–157
Gould G. W., Stubbs, J. M. & King W. L. (1970) *J. General Microbiology* 60, 347–355.
Wang, D. I. C. Scharer, J. G. & Humphrey A. E. (1964) *Applied Microbiol* 12 451–454.
Franklin J. G., Underwood, H. M., Perkin A. G. and Burton, H. (1970) *J. Dairy Res.* 37, 219–226. Hirsch, A. Grinsted, E. (1954) *J. Dairy Res.* 21, 101–110

EXAMPLE 1

Rate of kill of spores of Bacillus subtilis 706 by U. V. irradiation and hydrogen peroxide Spores of *Bacillus subtilis* 706 are irradiated as described above but in the presence or, for purposes of comparison, in the absence of a concentration of $H_2O_2$ (1 g/100 ml) which was previously found not to kill spores at comparable temperatures. In the absence of peroxide, irradiation produces a logarithmic rate of kill which results in 19 and 2% survivors after 30 and 60 sec. respectively. In the presence of peroxide, irradiation produces a much more rapid logarithmic kill so that after 30 sec. only 0.01% of spores survive.

EXAMPLES 2–16

Several strains of Bacillus and Clostridium are irradiated for 30 sec. In the presence of 2.5 g/100 ml $H_2O_2$ as described above followed by heating to 85° C. during 60 sec. The results are shown in Table 2 which also shows the results obtained from irradiation with U.V. alone and with U.V. followed by heat treatment.

TABLE 2

| Example | Strain | Survivors (%) U.V. alone* | U.V. and heat** | U.V. plus $H_2O_2$*** and heat |
|---|---|---|---|---|
| 2 | B. subtilis SA 22 | 1.44 | 0.23 | 0.0004 |
| 3 | B. licheniformis 109 2AO | 0.045 | 0.73 | 0.004 |
| 4 | B. globigii B17 (NCIB 8649) | 0.44 | 0.47 | 0.008 |
| 5 | B. stearothermophilus 202 (NCDO 1096) | 0.64 | 0.14 | 0.004 |
| 6 | B. pumilus 312 | 0.034 | 0.031 | 0.001 |
| 7 | B. subtilis 738 (NCDO 738: ATCC 9372) | 0.0053 | 0.022 | 0.002 |
| 8 | G12 | 0.067 | 0.00005 | 0.0009 |
| 9 | B. licheniformis 117 | 0.19 | 0.019 | 0.006 |
| 10 | B. subtilis 713 (NCDO 2130) | 0.89 | 0.005 | 0.006 |
| 11 | B. licheniformis 100 | 0.67 | 1.1 | 0.0003 |
| 12 | B. cereus 818 | 0.022 | 0.038 | <.0001 |
| 13 | B. cereus T | 0.020 | 0.0061 | 0.0001 |
| 14 | B. subtilis var. niger (NCIB 8058) | 0.14 | 0.61 | 0.002 |
| 15 | B. subtilis 706 (NCDO 2129) | 0.18 | 0.42 | 0.0008 |
| 16 | Clostridium sporogenes PA 3679 (NCIB 8053) | 0.21 | 0.0097 | <0.0001 |

*Lamp 5.5cm above spore suspension for 30 sec.
**Samples (2ml) removed and heated to 85° C. during 60 sec.
***Lamp 5.5cm above suspension with 2.5g peroxide/100ml for 30 sec. followed by heating to 85° C. during 60 sec.

EXAMPLES 17–24

*B. subtilis* 713 is irradiated with U.V. in the presence of varying concentrations of hydrogen peroxide at two different spore concentrations. The conditions and results are shown in Table 3.

TABLE 3

| Example | Hydrogen peroxide (g/100ml) | Survivors (%) after U.V. irradiation* $1.2 \times 10^7$/ml | $12 \times 10^7$/ml |
|---|---|---|---|
| 17 | 0 | 0.43 | |
| 18 | 0 | | 0.82 |
| 19 | 0.5 | 0.0073 | |
| 20 | 0.5 | | 0.39 |
| 21 | 1.0 | 0.0089 | |
| 22 | 1.0 | | 0.44 |
| 23 | 2.5 | 0.22 | |
| 24 | 2.5 | | 1.6 |

*Spores are suspended at $1.2 \times 10^7$ or $12 \times 10^7$/ml with hydrogen peroxide before irradiation with the U.V. lamp at 5.5cm above the suspension.

EXAMPLES 25–28

Four Bacillus strains are irradiated with U.V. in the presence of hydrogen peroxide and in two cases are subsequently heated to 85° C. over 60 sec. The conditions and results are shown in Table 4 which also shows for comparison purposes the results obtained from prior work using $H_2O_2$ without U.V. irradiation.

TABLE 4

Comparison of spore destruction by $H_2O_2$ and U.V. irradiation and by $H_2O_2$ alone.

| Strain | Ex. | $H_2O_2$ (g/100ml) | Temperature (°C.) | Time* (sec) |
|---|---|---|---|---|
| B. subtilis var. niger | — | 10 | 25 | 1800 Prior work |
|  | 25 | 1.0 + U.V. | 20 | 30 |
| B. subtilis 738 | — | 25.8 | 24 | 660 Prior work |
|  | 26 | 1.0 + U.V. | 20 | 30 |
| B. subtilis 713 | — | 3.0 | 90 | 600 Prior work |
|  | 27 | 2.5 + U.V. | 20 + 85** | 30 + 60** |
| B. licheniformis | — | 15 | 80 | 126 Prior work |
| 109 2AO | 28 | 2.5 + U.V. | 20 + 85** | 30 + 60** |

*Time is that required to produce a kill of 99.99%
**Spores irradiated at 20° for 30 sec. and then heated to 85° C. over 60 sec.

EXAMPLE 28

Spores of *B. subtilis* 706 are irradiated with U.V. for 60 sec. in the presence of $H_2O_2$ (1 g/100 ml). The U.V. lamp is located 30 cm above the spore suspension. For comparison purposes the strain is also irradiated with U.V. in the absence of $H_2O_2$. Samples are removed diluted and plated as hereinbefore described. The results are shown in Table 5.

TABLE 15

Destruction of spores of *B. subtilis* 706 by U.V.
Example: U.V. + $H_2O_2$
Comparison: U.V. only

| Irradiation Time (sec.) | Example Survivors % | Comparison Survivors % |
|---|---|---|
| 15 | 1.0 | — |
| 30 | 0.009 | 20 |
| 45 | 0.002 | 8 |
| 60 | 0.001 | 2 |

EXAMPLES 30–35

Spores of *B. pumilus* 312 are irradiated with U.V. for 30 sec. in the presence of $H_2O_2$ both with and without subsequent heating to 85° C. over 60 sec. The lamp is 5 cm above the suspension. For comparison purposes spores are incubated: (i) at 20° C. with hydrogen peroxide for 30 sec., (ii) with hydrogen peroxide for 30 sec. followed by heating to 85° C. over 60 sec. Samples are removed at intervals, diluted and plated as hereinbefore described. The results are shown in Table 6.

TABLE 6

Conditions:
Examples 30–32: U.V. + $H_2O_2$
(Comparison: $H_2O_2$)
Examples 33–35: U.V. + $H_2O_2$ + Heat
(Comparison: $H_2O_2$ + Heat)

| Example | Concentration of $H_2O_2$ | Survivors (%) (Examples) | Survivors (%) (Comparisons) |
|---|---|---|---|
| 30 | 0.25 | 0.04 | 90 |
| 30a | 0.50 | 0.02 | 80 |
| 30b | 0.75 | 0.01 | 100 |
| 31 | 1.0 | 0.01 | 100 |
| 32 | 1.75 | 0.3 | 80 |
| 32a | 2.50 | 0.5 | 100 |
| 33 | 0.25 | 0.01 | 100 |
| 33a | 0.50 | 0.002 | 80 |
| 33b | 0.75 | 0.001 | 50 |
| 34 | 1.0 | 0.0002 | 14 |
| 35 | 1.75 | 0.0002 | 0.13 |
| 35a | 2.50 | 0.0003 | 0.01 |

EXAMPLES 36–41

The procedure of Examples 30–35 is repeated using *B. subtilus* 713 in place of *B. pumilus* 312. The results are shown in Table 7.

TABLE 7

Conditions:
Examples 36–38: U.V. + $H_2O_2$
(Comparison: $H_2O_2$ only)
Examples 39–41: U.V. + $H_2O_2$ + Heat
(Comparison: $H_2O_2$ + Heat)

| Example | Concentration of $H_2O_2$ | Survivors (%) (Examples) | Survivors (%) (Comparisons) |
|---|---|---|---|
| 36 | 0.5 | 0.014 | 100 |
| 37 | 1.0 | 0.17 | 100 |
| 38 | 2.5 | 2.0 | 100 |
| 39 | 0.5 | 0.005 | 40 |
| 40 | 1.0 | 0.005 | 35 |
| 41 | 2.5 | 0.005 | 0.7 |

EXAMPLES 42–49

*E. coli* K-12 is irradiated with U.V. for 30 sec. in the presence of varying concentrations of hydrogen peroxide. The lamp is 30 cm above the suspension. For comparison purposes cells are also incubated for 30 sec. with 1 g/100 ml $H_2O_2$ in the absence of U.V. irradiation. Samples are removed, diluted and plated as hereinbefore described. The results are shown in Table 8.

TABLE 8

Conditions:
Examples 42–49: U.V. + $H_2O_2$
Comparison Experiment 50: $H_2O_2$ only.

| Example | Concentration of $H_2O_2$ | Survivors (%) (Examples) |
|---|---|---|
| 42 | 0.001 | 0.41 |
| 43 | 0.005 | 0.26 |
| 44 | 0.01 | 0.14 |
| 45 | 0.025 | 0.08 |
| 46 | 0.05 | 0.044 |
| 47 | 0.075 | 0.017 |
| 48 | 0.01 | 0.0085 |
| 49 | 0.25 | 0.0026 |
| 50 | 1.0 | 74 |

EXAMPLES 51–59

*S. faecalis* ss liquefaciens EB/F/30/39 is irradiated with U.V. for 30 sec. in the presence of varying concentrations of hydrogen peroxide. The lamp is 30 cm above the suspension. For comparison purposes cells are also incubated for 30 sec with 1.0 g/100 ml $H_2O_2$ in the absence of U.V. irradiation. Samples are removed diluted and plated as hereinbefore described. The results are shown in Table 9.

TABLE 9

Conditions:
Examples 51–59: U.V. + $H_2O_2$
(Comparison: 1g/100ml $H_2O_2$ only)

| Example | Concentration of $H_2O_2$ | Survivors (%) (Examples) | Survivors (%) (Comparison) |
|---|---|---|---|
| 51 | 0.001 | 1.0 | * |
| 52 | 0.005 | 0.7 | * |
| 53 | 0.01 | 0.6 | * |
| 54 | 0.025 | 0.32 | * |
| 55 | 0.05 | 0.29 | * |
| 56 | 0.1 | 0.11 | * |
| 57 | 0.5 | 0.026 | * |
| 58 | 0.75 | 0.024 | * |
| 59 | 1.0 | 0.011 | 100 |

*Not tested

EXAMPLES 60–61

Cells of *E. coli* K12 are irradiated with U.V. for 30 sec. in the presence of 1.0 g/100 ml $H_2O_2$ both with and without subsequent heating to 65° C. over 30 sec. The lamp is 30 cm above the suspension. For comparison purposes cells are (i) irradiated with U.V. for 30 sec. followed by incubation with $H_2O_2$ for 30 sec. (ii) heated to 65° C. over 30 sec. Samples are removed, diluted and plated as hereinbefore described. The results are shown in Table 10.

TABLE 10

Conditions:
Example 60: U.V. + $H_2O_2$
(Comparison: U.V. followed by $H_2O_2$)
Example 61: U.V. + $H_2O_2$ + heat
(Comparison: heat)

| Example | Concentration of $H_2O_2$ | Survivors (%) (Examples) | Survivors (%) (Comparisons) |
|---|---|---|---|
| 60 | 1.0 | 0.0044 | 0.14 |
| 61 | 1.0 | <0.00005 | 0.0013 |

EXAMPLES 62-69

Cells of *S. marcescens* are irradiated with U.V. for 30 sec. in the presence of varying concentrations of hydrogen peroxide. The lamp is 33 cm above the suspension. For comparison purposes cells are also incubated for 30 sec. with 1.0 g/100 ml $H_2O_2$ in the absence of U.V. irradiation. Samples are removed, diluted and plated as hereinbefore described. The results are shown in Table 11.

TABLE 11

Conditions:
Examples 62-69: U.V. + $H_2O_2$
(Comparison: 1.0g/100ml $H_2O_2$ only)

| Example | Concentration of $H_2O_2$ | Survivors (%) (Examples) | Survivors (%) (Comparison) |
|---|---|---|---|
| 62 | 0.01 | 0.046 | * |
| 63 | 0.025 | 0.022 | * |
| 64 | 0.05 | 0.014 | * |
| 65 | 0.1 | 0.011 | * |
| 66 | 0.25 | 0.0014 | * |
| 67 | 0.5 | 0.00095 | * |
| 68 | 0.75 | 0.00016 | * |
| 69 | 1.0 | <0.0001 | 86 |

*Not tested

EXAMPLES 70-71

Spores of *Penicillium chrysogenum* are irradiated with U.V. for 30 sec. in the presence of 0.5 g/100 ml $H_2O_2$ both with and without subsequent heating to 54° C. over 15 sec. The lamp is 5 cm above the suspension. For comparison purposes spores are (i) irradiated with U.V. for 30 sec. followed by incubation with $H_2O_2$ for 30 sec. (ii) heated to 54° C. over 15 sec. Samples are removed diluted and plated as hereinbefore described. The results are shown in Table 12.

TABLE 12

Conditions.
Example 70: U.V. + $H_2O_2$
(Comparison: U.V. followed by $H_2O_2$)
Example 71: U.V. + $H_2O_2$ + heat
(Comparison: heat)

| Example | Concentration of $H_2O_2$ | Survivors (%) | Survivors (%) |
|---|---|---|---|
| 70 | 0.5 | 0.95 | 3.3 |
| 71 | 0.5 | 0.0033 | 9.6 |

We claim:

1. A method of sterilizing food packaging which comprises treating a microorganism at the surface of the packaging with an ultraviolet irradiated solution of hydrogen peroxide, the wavelength of the ultraviolet radiation being wholly or predominantly below 325 nm and the concentration of the hydrogen peroxide being at least 0.01% and no greater than 10% by weight, whereby the microorganism is rendered non-viable by synergism between the radiation and the hydrogen peroxide.

2. A method according to claim 1 in which the wavelength of the ultraviolet radiation is wholly or predominantly below 300 nm.

3. A method according to claim 1 in which the radiation has a peak intensity below 325 nm.

4. A method according to any of claims 1-3 in which the wavelength of the ultraviolet radiation is at least 200 nm.

5. A method according to any of claims 1-3 in which the ultraviolet radiation has a peak intensity at 254 nm.

6. A method according to any of claims 1-3 in which the concentration of the hydrogen peroxide solution is at least 0.5% by weight.

7. A method according to any of claims 1-3 in which the concentration of the hydrogen peroxide solution is no greater than 6% by weight.

8. A method according to any of claims 1-3 in which the concentration of the hydrogen peroxide solution is no greater than 3% by weight.

9. A method according to any of claims 1-3 in which the microorgaism is present in the form of spores and the concentration of hydrogen peroxide is at least 0.25%.

10. A method according to any of claims 1-3 in which the microorganism is a mould, yeast, bacterium, virus or protozoa.

11. A method according to any of the claims 1-3 in which the microorganism is a dairy contaminant.

12. A method according to claim 10 in which the microorganism is present in the form of spores of *B. subtilis* or *B. stearothermophilus*.

13. A method according to any of claims 1-3 in which the hydrogen peroxide is maintained at an elevated temperature during or subsequent to irradiation.

14. A method according to any of claims 1-3 in which the hydrogen peroxide solution is maintained at at least 85° C. during or subsequent to irradiation.

15. A method according to any of claims 1-3 in which the hydrogen peroxide solution is heated for at least 10 seconds during or subsequent to irradiation.

16. Food packaging material when sterilised according to the method of claim 1.

17. A method of sterilisation which comprises treating spores of a microoganism with an ultraviolet irradiated solution of hydrogen peroxide, the wavelength of the ultraviolet radiation having a peak intensity within the range 200-325 nm and the concentration of the hydrogen peroxide being at least 0.5% and no greater than 3% by weight, whereby the microorganism is rendered non-viable by synergism between the radiation and hydrogen peroxide.

18. Food packaging material when sterilised according to the method of claim 17.

* * * * *